United States Patent
Bhat

(10) Patent No.: US 7,060,494 B2
(45) Date of Patent: *Jun. 13, 2006

(54) GROWTH OF HUMAN MESENCHYMAL STEM CELLS (HMSC) USING UMBILICAL CORD BLOOD SERUM AND THE METHOD FOR THE PREPARATION THEREOF

(75) Inventor: Aravind Venkatrao Bhat, Mumnai (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 481 days.

This patent is subject to a terminal disclaimer.

(21) Appl. No.: 10/409,458

(22) Filed: Apr. 8, 2003

(65) Prior Publication Data

US 2003/0232432 A1 Dec. 18, 2003

Related U.S. Application Data

(60) Provisional application No. 60/371,137, filed on Apr. 9, 2002.

(51) Int. Cl.
*C12N 5/00* (2006.01)

(52) U.S. Cl. .................. 435/366; 435/325; 435/372; 435/377

(58) Field of Classification Search ................ 435/325, 435/366, 372, 377
See application file for complete search history.

(56) References Cited

U.S. PATENT DOCUMENTS 5,827,740 A * 10/1998 Pittenger .................... 435/372
5,994,126 A * 11/1999 Steinman et al. ........... 435/325
6,322,784 B1 * 11/2001 Pittenger et al. ........... 424/93.7
2003/0219866 A1 * 11/2003 Kruijer ...................... 435/69.1

* cited by examiner

*Primary Examiner*—Leon B. Lankford, Jr.
(74) *Attorney, Agent, or Firm*—Lackenbach Siegel, LLP

(57) ABSTRACT

A method of isolating and growing human mesenchymal stem calls (hMSC) by culturing human stem cells in human umbilical cord blood serum. For this purpose blood is collected from the umbilical cord at the time of birth, after the infant is separated from the umbilical cord, and the blood is collected from an umbilical vein free of anticoagulants. The blood is collected in a blood bag having a collecting needle which is inserted into the umbilical vein and the blood is allowed to flow from the vein into the blood bag, and the blood is allowed to clot at room temperature and the bag is transported to a processing area which is a cGMP clean room. The method also includes aspirating Human Mesenchymal Stem Cells (hMSC) present in bone marrow, diluting bone marrow aspirate with tissue culture medium; plating cell suspension into tissue culture flasks so that Human Mesenchymal Stem Cells (hMSC) can adhere for 24 hours; transferring the resulting supernatant to fresh flasks for the remaining Human Mesenchymal Stem Cells (hMSC) to adhere, feeding cultures every 3 days using the medium and cultures reach confluence by 3 weeks, adding 5-aza cytidine reagent to these cultures at final concentration of 5–20 micro molars and allowing the culture to grow for another 3 days.

20 Claims, No Drawings

GROWTH OF HUMAN MESENCHYMAL STEM CELLS (HMSC) USING UMBILICAL CORD BLOOD SERUM AND THE METHOD FOR THE PREPARATION THEREOF

CROSS REFERENCE TO RELATED APPLICATION

This application claims priority from provisional U.S. provisional patent application filed Apr. 9, 2002 under Ser. No. 60/371,137.

TECHNICAL FIELD

The present invention provides the use of sera or serum separated from the clotted umbilical cord blood for growing human stem cells and adult cells for therapeutic purposes in regenerative medicine. In particular, the present invention relates to the growth of Human Mesenchymal Stem Cells (hMSC) and a method for preparation thereof using cord blood serum, for therapeutic purposes.

BACKGROUND OF THE INVENTION

Stem cells are special cells that have the ability to develop into many different types of tissue: bone, muscle, nerve, etc. In theory, they could be grown into replacements for almost any part of the human body. Stem cells are typically found in the embryo and umbilical cord of an organism, and in reservoirs within the human body. Researchers hope that stem cells will provide a solution to cure diseases caused by cell failure, and for repairing tissues that do not repair themselves. Heart damage, spinal cord injuries, Parkinson's disease, leukemia, and diabetes are among diseases named in relation to stem cell research. Hence, researchers are of the opinion, if these stem cells are controlled, they could cure a variety of debilitating diseases in the years to come. Stem cells are separated into three (3) distinct categories viz. Totipotent, Pluripotent, and Multipotent. Stem cells are best described in relation to normal human development. Thus, a fertilized egg is totipotent. It produces an entire organism. After several cycles of cell division, these totipotent cells begin to specialize, becoming pluripotent. As the embryo begins to develop, these pluripotent cells become multipotent, specifically producing blood, skin, nerve, or other types of body cells. While stem cells are extraordinarily important in early human development, multipotent stem cells are also found in children and adults. For example, one of the best understood stem cells are the blood stem cells. Blood stem cells reside in the bone marrow of every child and adult, and in fact, they can be found in very small numbers circulating in the blood stream. Blood stem cells perform the critical role of continually replenishing the supply of blood cells—red blood cells, white blood cells, and platelets throughout the life span.

Stem cells are the building blocks of blood and immune systems. They form the white cells that fight infection, the red cells that carry oxygen and platelets that promote clotting. Stem cells are normally found in bone marrow where they continue to generate new blood cells throughout the life span of an individual. The presence of these stem cells in the bone marrow, has made marrow transplantation an important therapeutic modality in the treatment of variety of malignant and non-malignant diseases. This is because of the realization that permanent clinical benefit from transfused blood cells can come from transplantation of multipotent haematopoietic stem cells. Besides bone marrow, Mobilized Peripheral Blood (MPB), and Umbilical Cord Blood (UCB) have also been used successfully for transplantation. In recent years although significant advances have been made in bone marrow transplantation (BMT), the basic problem of finding a suitable matching donor still remains. This is because a group of antigens expressed by the leukocytes called the human leukocyte antigens (HLA) need to match between the donor and the recipient. Further bone marrow harvesting is a painful and invasive procedure and many donors are unwilling to donate marrow. Therefore, the search for alternate sources of stem cells has led to the development of stem cell transplant protocols from different tissues like liver (Kochupillai 1991), mobilized peripheral blood (Benboubker 1995), and cord blood (Mayani 1998). Of these, cord blood has significant advantages over the others. Increasingly, experts say cord blood transplants have distinct advantages over more traditional bone marrow transplants in stimulating the growth of healthy white blood cells. Stem cells can be collected from the bone marrow. However, the collection procedure is invasive, time-consuming, requires an anaesthetic and is painful for the donor. Also, cord blood is easily available, involves a non invasive collection procedure and is better tolerated in transplants across the HLA barrier.

Like bone marrow, umbilical cord blood is rich in stem cells. Umbilical Cord Blood is the blood that remains in the placenta and umbilical cord following birth. Until recently the placenta and umbilical cord were discarded after delivery as medical waste, but now research has shown that cord blood is a rich source of blood (haematopoetic) stem cells, which can be collected, processed and frozen for potential future use. An experimental procedure to use umbilical cord blood instead of bone marrow to treat immune diseases is gaining attention from doctors and patients.

In the face of extraordinary advances in the prevention, diagnosis, and treatment of human diseases, devastating illnesses such as heart disease, diabetes, cancer, and diseases of the nervous system, such as Parkinson's Disease and Alzheimer's Disease, continue to deprive people of health, independence, and well-being. Research in human developmental biology has led to the discovery of human stem cells (precursor cells that can give rise to multiple tissue types), including embryonic stem (ES) cells, embryonic germ (EG) cells, fetal stem cells, and adult stem cells. Recently, techniques have been developed for the in vitro culture of stem cells, providing unprecedented opportunities for studying and understanding human embryology. As a result, scientists can now carry out experiments aimed at determining the mechanisms underlying the conversion of a single, undifferentiated cell, the fertilized egg, into the different cells comprising the organs and tissues of the human body. Although it is impossible to predict the outcomes, scientists and the public will gain immense new knowledge in the biology of human development that will likely hold remarkable potential for therapies and cures.

Human Mesenchymal Stem Cells are adult stem cells that are present in bone marrow stroma. They are a heterogeneous population which have been well characterized in their ability to proliferate in culture and differentiate into multiple mesechymal lineages under controlled conditions.

Until the present, Human Mesenchymal Stem Cells are being cultured in animal serum such as Fetal Bovine Serum (FBS), Human adult blood serum or a complex mixture of growth factors derived by mixing purified factors which are either isolated from FBS or Human Adult blood serum or a mixture of growth factors derived from recombinant methods.

However, these conventional culture media are associated with shortcomings and risks.

Stem cells from adult/fetal as well as other sources are being widely used to regenerate tissues in patients after they have degenerated. For this purpose, these cells have to be grown in the tissue culture for varying periods of time using defined media, the principle constituent of which is animal serum such as Fetal Bovine Serum (FBS).

FBS is the most widely used serum in the culturing of cells, tissues and organs in vitro, in industry, medicine, and science. FBS has been shown to be essential for adhesion, proliferation and differentiation of the cells. However, animal serum such as FBS can be infected with several pathogens such as prions. Several known and unknown viruses may be present in the serum. Therefore cells/tissue cultured in the presence of FBS get infected and transmit these pathogens to the patient on transplantation. As stated FBS may have known and unknown pathogens which may get transmitted to the human transplant subject, if these cells are grown in FBS. The pathogens present in FBS are difficult to screen for likely causative agents of diseases in humans. Hence, using such cells in a human can be life threatening as there is every chance of a pathogen getting transmitted along with these cells.

Human adult blood serum also supports growth of several cells, however, it cannot substitute for FBS. Moreover, it is difficult to harvest large amounts of serum from Human adult blood. Hence, it is not widely used for culturing of cells, tissues and organs in vitro.

Several investigators have tried to use a combination of complex mixture of growth factors which are known to influence growth and differentiation of stem cells. However, the success is limited and it has been shown conclusively that at least 2% v/v of the tissue culture media should be made up of FBS for optimal growth of the cells.

There is a dire need to find an adequate substitute for conventional culture media for growing Human Mesenchymal Stem Cells. Looking to the need of the hour, the present inventors have resolved the above issue of concern and have come out with a solution which will be of utmost importance in the field of regenerative medicine. The inventors have come out with a unique component for culturing Human Mesenchymal Stem Cells. The present invention is advantageous over the prior art as it obviates the problems associated with the conventional culture media for growing Human Mesenchymal Stem Cells.

The present invention has solved the problem by culturing human stem cells in umbilical cord blood serum. Cord blood being a natural substance, is found to be rich in growth factors. Taking this factor in mind, the inventors of the present invention, have investigated a method of growing Human Mesenchymal Stem Cells in cord blood serum.

Use of umbilical cord blood in haematopoietic reconstitution has been around since 1970. However, no work has been done in using umbilical cord blood as a source for growing Human Mesenchymal Stem Cells. The inventors of the present invention have been successful in discovering this novel source for growing Human Mesenchymal Stem Cells.

OBJECTS OF THE INVENTION

It is an object of the present invention to grow human stem cells and adult cells using umbilical cord blood serum for therapeutic purposes in regenerative medicine.

It is a further object of the present invention to grow Human Mesenchymal Stem Cells (hMSC) using cord blood serum.

It is still a further object of the present invention to develop a method for growing Human Mesenchymal Stem Cells (hMSC) using cord blood serum for therapeutic purposes.

SUMMARY OF THE INVENTION

In accordance with one aspect of this invention, there is provided the use umbilical cord blood sera for growing human stem cells and adult cells, like Human Mesenchymal Stem Cells (hMSC) for therapeutic purposes in regenerative medicine.

To overcome the major obstacle described above, the inventors of the present invention have conducted research on human umbilical cord blood and have replaced conventionally used Fetal Bovine Serum (FBS) by cord blood serum.

As stated, Human umbilical cord blood is a fetal product and a waste product during childbirth. During the gestation of the child in the mother's womb, the placenta and the blood present in the placenta nourish the developing foetus and are therefore rich in several growth promoting factors. The inventors of the present invention have taken advantage of this property of Human umbilical cord blood serum and have substituted it for FBS.

The procedure by which Human umbilical cord blood is collected is given below. It is serum from this cord blood that is used for growing Mesenchymal Stem Cells (MSC) of the present invention.

Preparation of Umbilical Cord Blood Serum.

Umbilical cord blood is collected at the time to birth from pre-screened mothers for infectitious disease causing organisms, such as HIV 1 and 2, Hbs and HCV and sexually transmitted diseases. The collection is made after the baby is separated from the clamped cord; therefore, there is no harm to the baby. Blood is collected from umbilical vein using the conventional blood bag containing no anticoagulants. The needle of the bag is inserted in to the vein and blood is allowed to flow into the blood bag. A good collection can exceed 100 ml. This blood is now allowed to clot at room temperature and is transported to the processing area, which is a cGMP clean room. The clotting process is allowed to take place up to 8 hours or overnight. The blood is then centrifuged at 1000 g in a blood bag centrifuge and the clear serum is collected into sterile containers. The serum is now tested for sterility by microbiological assays for aerobic or anaerobic microorganisms. The complement is inactivated by keeping sera at 56° C. for ½ hour.

Serum is aliquoted into 10 ml sterile vials and capped. Lot number and Batch number are fixed on it.

Growth of Human Mesenchymal Stem Cells (hMSC) using Human Umbilical Cord Blood Serum as Prepared by the Procedure Given Above.

In accordance with a second aspect of this invention, the inventors of the present invention have come out with the invention of growing Human Mesenchymal Stem Cells (hMSC) using cord blood serum and a method for preparation thereof for therapeutic purposes.

Mesenchymal Stem Cells are multipotent cells that can be isolated from adult bone marrow and can be induced in in vitro and in vivo to differentiate into a variety of mesenchymal tissues, including bone, cartilage, tendon, fat, bone marrow stroma, and muscle.

Despite advances in the treatment of myocardial infarction (MI), congestive heart failure secondary to infarction continues to be a major complication. The cardiomyoctyes lost during an MI cannot be regenerated, and the extent of the loss is inversely related to cardiac output, pressure-generating capacity, and ultimately survival.

Cell therapy, or the supplementation of tissue with exogenous cells, has previously been used in the treatment of disease in which terminally differentiated cells are irreparably damaged. Recently, it has been suggested that cell therapy with myoblasts may be effective in the treatment of MI. Cell therapy has been used effectively in the treatment of a variety of human disorders from Parkinson's disease to diabetes, and holds promise in the therapy of many diseases in which non-regenerative cell death or abnormal cellular function plays a role.

The present invention is also directed to a method of isolation of Human Mesenchymal Stem Cells (hMSC) comprising of the following.

a) aspirating Human Mesenchymal Stem Cells (hMSC) present in bone marrow under sterile conditions by qualified medical personnel; b) bone marrow aspirates are further processed for enrichment, expansion and differentiation of Human Mesenchymal Stem Cells (hMSC) towards muscle pre-cursors; c) diluting bone marrow aspirate with tissue culture medium, Dulbecco's modified essential medium (DMEM) and Ham's F-12 in the ratio 1:1 and fortifying with 10–30% human umbilical cord blood serum; d) the cell suspension is plated into tissue culture flasks so that Human Mesenchymal Stem Cells (hMSC) can adhere for 24 hours; e) transferring the resulting supernatant to fresh flasks for the remaining Human Mesenchymal Stem Cells (hMSC) to adhere, three such passages are made and these cultures are incubated at 37° C. in $CO_2$ incubator with 5% carbon dioxide in air; f) cultures are fed every 3 days using the medium described above, cultures reach confluence by 3 weeks; g) at this point 5-aza cytidine reagent is added to these cultures at final concentration of 5–20 micro molars; h) the culture is allowed to grow for another 3 days and the is used for harvesting/implantation in patients.

Human Mesenchymal Stem Cells (hMSC) isolated by the present invention, are used to reconstruct damaged myocardium in patients who have undergone multiple myocardial infarcts, which has resulted in loss of cardiac muscles. Such a heart has low function and is potentially life threatening as the cardiomyocytes lost during an myocardial infarcts cannot be regenerated, and the extent of the loss is inversely related to cardiac output, pressure-generating capacity, and ultimately survival. Cultured and differentiated Human Mesenchymal Stem Cells (hMSC) of the present invention, are implanted during heart surgery or using a catheter into the damaged myocardium, where they grow and transform themselves into heart muscles. This procedure improves the function of the heart.

Conventionally, patients have to be transplanted with a healthy heart from a donor who is tissue matched. Unfortunately, such donors are not easily available and the procedure is not very successful in improving the patient's life. However, the present procedure suggest that use of Human Mesenchymal Stem Cells (hMSC) derived cardiomyocytes grown in umbilical cord blood serum will be beneficial for cellular transplantation therapy of myocardial infarction in humans is technically feasible.

In view of the foregoing descriptions, it will become apparent to those skilled in the art that equivalent modifications thereof may be made without departing from the spirit and scope of this invention.

The invention claimed is:

1. A method of growing human mesenchymal stem cells (hMSC) for therapeutic purposes in regenerative medicine comprising the steps of:
   a. separation of umbilical cord and collecting the umbilical cord blood;
   b. isolating the serum from the umbilical cord blood; and,
   c. culturing human stem cells in umbilical cord blood serum.

2. The method as claimed in claim 1, including the step of collecting blood from the umbilical cord at the time of birth.

3. The method as claimed in claim 1, including the step of separating an infant from the umbilical cord; and collecting the blood from an umbilical vein free of anticoagulants.

4. The method as claimed in claim 3, including
   collecting the blood in a blood bag having a collecting needle; and
   inserting the collecting needle into the umbilical vein and allowing the blood to flow from the vein into the blood bag.

5. The method as claimed in claim 4, including allowing the blood to clot at room temperature and transporting the bag to a processing area which is a cGMP clean room.

6. The method as claimed in claim 5, wherein the blood is allowed to clot up to about eight hours and then centrifuged at 1000 g in a blood bag centrifuge.

7. The method as claimed in claim 6, including collecting the clear serum in a sterile container, and inactivating the complement by keeping the sera at 50° C. for ½ hour.

8. The method as claimed in claim 5, including obtaining blood from the umbilical cord at the time of birth and allowing the blood to clot and then centrifuging the blood at 1000 g in a blood bag centrifuge.

9. The method as claimed in claim 3, wherein the blood is collected and placed into a conventional blood bag having a collecting needle.

10. The method as claimed in claim 7, including aliquoting the serum into 10 ml sterile vials and capping them.

11. A method of isolating Human Mesenchymal Stem Cells (hMSC) comprising the steps of:
    aspirating Human Mesenchymal Stem Cells (hMSC) present in bone marrow;
    diluting bone marrow aspirate with tissue culture medium comprising umbilical cord blood serum;
    plating cell suspension into tissue culture flasks so that Human Mesenchymal Stem Cells (hMSC) can adhere for 24 hours;
    transferring the resulting supernatant to fresh flasks for the remaining Human Mesenchymal Stem Cells (hMSC) to adhere;
    feeding cultures every 3 days using the medium and cultures reach confluence by 3 weeks;
    adding 5-aza cytidine reagent to these cultures at final concentration of 5–20 micro molars; and
    allowing the culture to grow for another 3 days.

12. The method as claimed in claim 11, wherein the bone marrow aspirate is diluted with tissue culture medium, dulbecco's modified essential medium (DMEM) and Ham's F-12 in the ratio 1:1 and fortified with 10–30% human umbilical cord blood serum.

13. The method as claimed in claim 11, including further processing the bone marrow aspirates for enrichment, expansion and differentiation of Human Mesenchymal stem cells (hMSC) towards muscle precursors.

14. The method as claimed in claim 11, wherein three passages are made of the resultant supernatant cultures and incubating the cultures at 37° in $CO_2$ with 5% carbon dioxide in air.

15. The method as claimed in claim 13, including making three passages of the resulting supernatant cultures, and incubating the supernatant cultures at 37° in $CO_2$ incubator with 5% carbon dioxide in air.

16. The method as claimed in claim 15, including aliquoting the serum into 10 ml sterile vials and capping them.

17. The method according to claim 11 of using sera or serum separated from a clotted umbilical cord blood for growing human stem cells and adult cells for therapeutic purposes in regenerative medicine comprising obtaining non-infected blood after severance of the umbilical cord from a newborn infant.

18. The method of growing Human Mesenchymal stem cells (hMSC) and for preparation thereof using cord blood for therapeutic purposes as claimed in clam 17, comprising using umbilical cord blood sera for growing human stem cells and adult cells for therapeutic purposes in regenerative medicine.

19. The method of growing Human Mesenchymal stem cells (hMSC) and for preparation thereof using cord blood for therapeutic purposes as claimed in claim 11, comprising using umbilical cord blood sera for growing human stem cells and adult cells for therapeutic purposes in regenerative medicine.

20. A method of isolating Human Mesenchymal Stem Cells (hMSC) free of Fetal Bovine serum (FBS) comprising the use of sera separated from clotted umbilical cord blood for growing human stem cells including steps of:

aspirating Human Mesenchymal Stem Cells (hMSC) present in bone marrow;

diluting bone marrow aspirate with tissue culture medium comprising umbilical cord blood serum;

plating cell suspension into tissue culture flasks so that Human Mesenchymal Stem Cells (hMSC) can adhere for 24 hours; transferring the resulting supernatant to fresh flasks for the remaining Human Mesenchymal Stem Cells (hMSC) to adhere; and feeding cultures every 3 days using the medium and cultures reach confluence by 3 weeks; adding 5-aza cytidine reagent to these cultures at final concentration of 5–20 micro molars.

* * * * *